United States Patent [19]

DeCamp et al.

[11] Patent Number: 5,064,964

[45] Date of Patent: Nov. 12, 1991

[54] PROCESS FOR CERTAIN (2R-TRANS)HEXAHYDROAROQUINOLIZINES

[75] Inventors: Ann E. DeCamp, North Plainfield; Anthony O. King, Colonia; Ralph P. Volante, East Windsor; Ichiro Shinkai, Westfield, all of N.J.

[73] Assignee: Merck & Co., Inc., Rahway, N.J.

[21] Appl. No.: 506,056

[22] Filed: Apr. 9, 1990

Related U.S. Application Data

[62] Division of Ser. No. 324,138, Mar. 16, 1989, Pat. No. 4,942,235.

[51] Int. Cl.$^5$ .......................................... C07D 221/18
[52] U.S. Cl. ........................................ 546/48; 546/50; 546/62; 546/64
[58] Field of Search ..................... 546/48, 62, 50, 64

[56] References Cited

U.S. PATENT DOCUMENTS 4,831,035 5/1989 Baldwin et al. ...................... 546/18
4,916,233 4/1990 Baldwin et al. ...................... 546/18

FOREIGN PATENT DOCUMENTS 876400 4/1988 South Africa ...................... 546/20

*Primary Examiner*—Mukund J. Shah
*Assistant Examiner*—E. C. Ward
*Attorney, Agent, or Firm*—Alice O. Robertson; Hesna J. Pfeiffer

[57] ABSTRACT

A unique process for preparing certain (2R-trans)hexahydroaroquinolizines, especially (2R-trans)-N-[2-(1,3,4,6,7,12b-hexahydro-2'-oxospiro[aro-[2,3-a]-quinolizine-2,4'-imidazolidin]-3'-yl) ethyl)-methanesulfonamide from (2R-trans)-N-[2-[(2-cyano-(1,3,4,6,7,12b-hexahydro-aro-[2,3-a]quinolizin-2-yl)amino]ethyl]methanesulfonamide is described.

2 Claims, No Drawings

PROCESS FOR CERTAIN (2R-TRANS)HEXAHYDROAROQUINOLIZINES

This is a division of application Ser. No. 07/324,138, filed Mar. 16, 1989, now U.S. Pat. No. 4,942,235.

The present invention is to an improved process for preparing certain (2R-trans)-hexahydroaroquinolizines, especially (2R-trans)-N-[2-(1,3,4,6,7,12b-hexahydro-2'-oxospiro[2H-aro-[2,3-a]-quinolizine-2,4'-imidazolidin]-3'-yl)ethyl]methanesulfonamide.

BACKGROUND OF THE INVENTION (2R-trans)-N-[2-(1,3,4,6,7,12b-hexahydro-2'-oxospiro[2H-benzofuro[2,3-a]quinolizine-2,4'-imidazolidin]-3'-yl)ethyl]methanesulfonamide and certain other (2R-trans)hexahydroaroquinolizines which may be named (2R-trans)-N-(2-(1,3,4,6,7,12b-hexahydro-2' -oxosphiro[2H-aro[2,3-a]quinolizine-2,4'-imidazolidin]-3'yl)ethyl)methanesulfonamide and represented by the formula

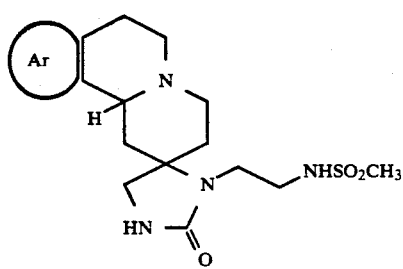

(I)

wherein

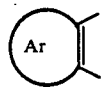

is an aromatic ring system as hereinafter defined are peripherally selective $\alpha_2$-adrenoceptor antagonists. As peripherally selective $\alpha_2$-adrenoceptor antagonists, they are adapted to be employed for the treatment of certain pathological disorders, such as hypertension, diabetes, obesity disorders involving platelet aggregation and gastrointestinal motility and the like, without side effects attributable to the effect of the drug on the central nervous system. They have been found to be especially useful in the treatment of diabetes.

In the foregoing formula,

is a divalent radical of an aromatic ring system selected from

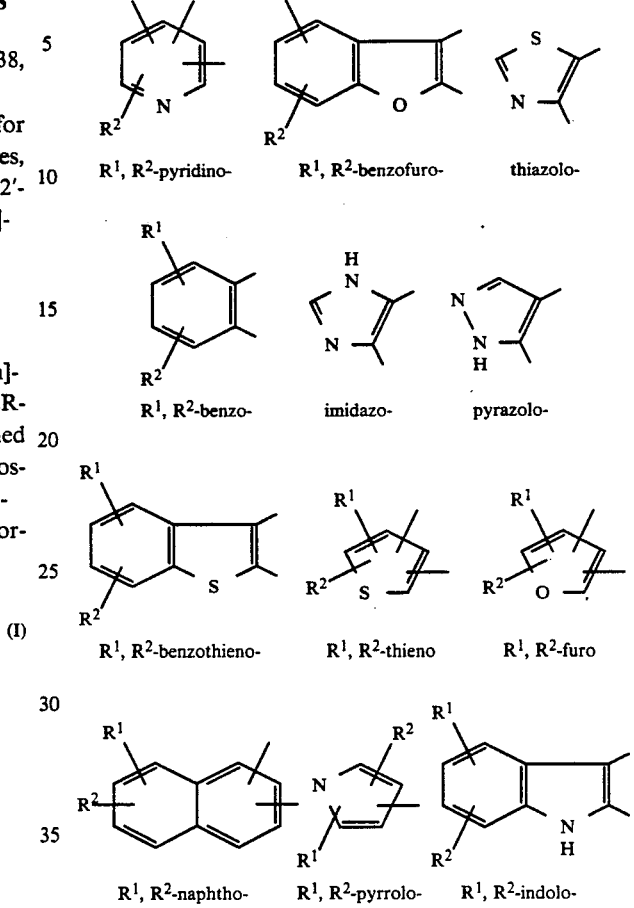

wherein $R^1$ and $R^2$ are independently hydrogen, halo, hydroxy, $C_{1-3}$ alkoxy, lower alkyl or carboxy, or together are methylenedioxy or $C_{3-4}$ alkylene; and wherein the free bonds of Ar are attached to the quinolizine ring in either configuration of Ar.

The compounds of formula (I) are included in those disclosed in copending application Ser. No. 76,495, filed July 27, 1987, which is a continuation-in-part application of U.S. Ser. No. 901,485, filed Aug. 28, 1986, now abandoned. The application issued into South African Patent 87/6400 on Apr. 27, 1988.

In the present application, the compounds of formula (I) are referred to as (2R-trans)-N-[2-(1,3,4,6,7,12b-hexahydro-2'-oxospiro[2H-aro-[2,3-a]-quinolizine-2,4'-imidazolidin]-3'-yl)ethyl]methanesulfonamide. This is a preferred Chemical Abstracts nomenclature. In the aforementioned copending application and South African patent, the nomenclature employed to designate the compounds represented by formula (I) would be (2R,12bS)-3'-(2-methanesulfonamideoethyl)-spiro-[1,3,4,6,7,12b -hexahydroaro-[2,3-a]quinolizin]-2,4'-imidazolidin-2-one. Thus, one of the compounds in the aforementioned South African patent, in which the "aro" group is "benzofuro" and having the formula:

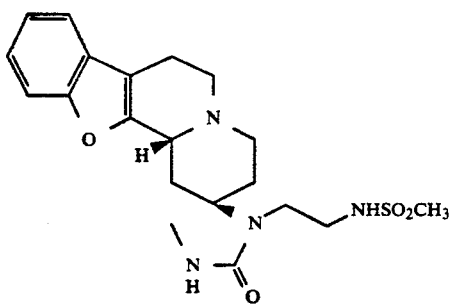

would be named, using the Chemical Abstracts nomenclature, (2R-trans)-N-[2-(1,3,4,6,7,12b-hexahydro-2'-oxospiro[2H-aro[2,3-a]quinolizine-2,4'imidazolidin]-3'-yl)ethyl]methanesulfonamide but would be named in accordance with the nomenclature used in the patent as (2R,12bS)-3'-(2-methanesulfonamidoethyl)-spiro-[1,3,4,6,7,12b-hexahydrobenzo[b]furo[furo[2,3-a]quinolizin]-2,4'-imidazolin-2'-one.

In the latter patent may be found described a process for the preparation of the compounds. The preparation requires a number of steps and includes certain steps which are not adaptable to large scale synthesis.

The process described in the foregoing patent may be represented by the following flow diagram:

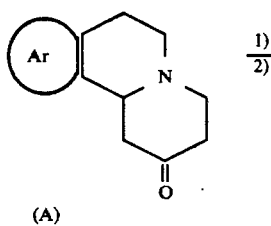 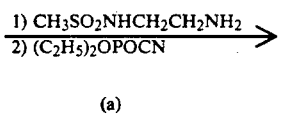

(A)

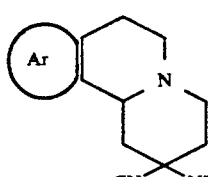 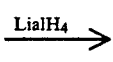

(B)

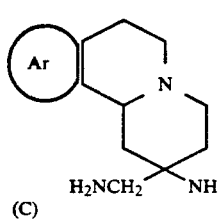 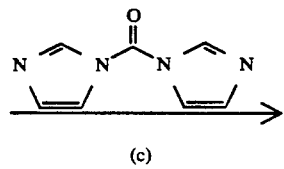

(C)

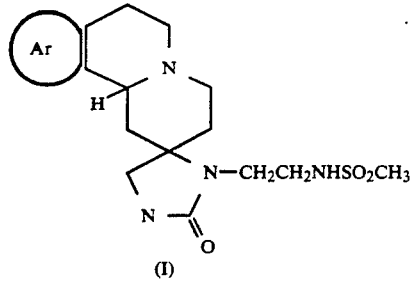

(I)

Thus, in accordance with the foregoing flow diagram, a quinolizin-2-one compound (A) and a 2-aminoethylmethanesulfonamide are caused to react in methanolic tetrahydrofuran, followed by the reaction of the product with diethyl cyanophosphonate to obtain in accordance with Step (a), an intermediate Compound B which after recovery and purification by chromatography is reduced with lithium aluminum hydride according to Step (b) to obtain intermediate Compound C. Compound C, after purification by chromatography, is caused to react with carbonyldiimidazole (Step (c)) to obtain Compound I. The latter is then recovered and purified by chromatography.

The process employing the foregoing sequence of reactions is not suitable for large scale preparation and/or manufacturing. Thus, initially, chromatography which is used in most steps of the published synthesis is not generally appropriate or practical for purification on a large scale. Crystallization is a useful purification method adaptable to large scale preparations; thus where possible, compounds are converted to their salts which generally form crystals readily. Thus, in the foregoing flow diagram, Compound B may be purified on a large scale by forming an acid addition salt such as a bis hydrogen chloride addition salt. However, in order to carry out the next step, the hydrogen chloride addition salt, must be converted back to the free base. Conversion to the free base is accompanied by decomposition and hydrolysis with losses of about 15 percent or even higher. The free base decomposes into an imine of the structure:

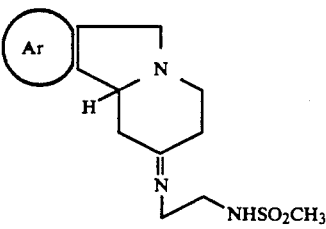

or its hydrolysis product which is the starting material, Compound A. These by-products give rise in the next reduction step to the following compounds:

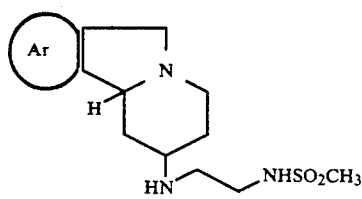

-continued and

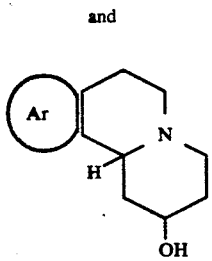

which are difficult to separate from the desired intermediate Compound C.

Moreover, in Step (b), the lithium aluminum hydride used as reducing agent is undesirable on a large scale because of the hazardous nature of reactions when large amounts of this reducing agent are employed. Other reagents providing less hazardous reaction conditions are ineffective for this reaction. In addition, the isolation of Intermediate C from the reaction mixture after a lithium aluminum hydride reduction is extremely difficult on a large scale because of binding by the amine groups to the aluminum by-products.

Thus, it is desirable to find a more efficient and safe process for proceeding from Compound A to the desired Compound I.

STATEMENT OF INVENTION

According to the present invention there has been discovered an improved process for the preparation of (2R-trans)-N-(2-(1,3,4,6,7,12b-hexahydro-2'-oxospiro[2H-aro[2,3-a]-quinolizine-2,4'-imidazolidin]-3'-yl)ethyl)methanesulfonamide.

DESCRIPTION OF THE INVENTION

The process of the present invention for facilely producing (2R-trans)-N-(2-(1,3,4,6,7,12b-hexahydro-2'-oxospiro[2H-aro[2,3-a]quinolizine-2,4'-imidozalidin]-3'-yl)ethyl)methanesulfonamide (I) comprises the following sequence of reactions:

1) intimately contacting (2R-trans)-[2-[(2-cyano-1,3,4,6,7,12b-hexahydro-aro[2,3-a]quinolizine-2-yl)-amino]ethyl]methanesulfonamide bis-hydrochloride (Compound B•2HCl) with carbonyldiimidazole in the presence of 1,8-diazabicyclo[5.4.0]undec-7-ene to obtain a novel intermediate, (trans)-1,3,4,6,7,12b-hexahydro-2-3-(methylsulfonyl)-2-oxo-1-imidazolidinyl]-2H-Benzofuro[2,3-a]quinolizine-2-carbonitrile (Compound D);

2) intimately contacting (trans)-1,3,4,6,7,12b-hexahydro-2-[3-(methanesulfonyl)-2-oxo-1-imidazolidinyl]-2H-aro[2,3-a]quino-lizine-2-carbontrile with hydrogen in the presence of Raney nickel catalyst and sodium methoxide to obtain (2R-trans)-N-[2-(1,3,4,6,7,12b-hexahydro-2'-oxospiro[2H-aro[2,3-a]-quinolizine-2,4'-imidazolidin)-3'-yl)ethylmethanesulfonamide and then contacting said methanesulfonamide with methanol and acetyl chloride to obtain the monohydrochloride thereof (Compound I•HCl). The foregoing steps may be illustrated in the following flow diagram:

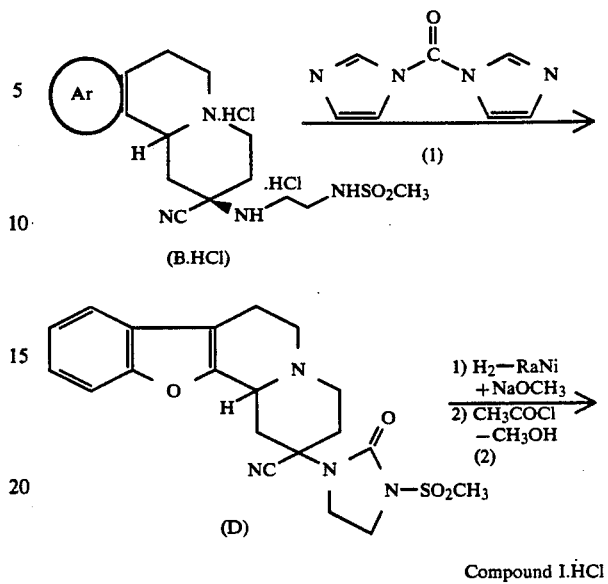

(2R-trans)-[2-[(2-cyano-1,3,4,6,7,12b-hexahydro-2H-aro-[2,3-a]quinolizine-2-yl)-amino]ethyl]methanesulfonamide bis-hydrochloride, Compound B.2HCl, which is the starting material for the sequence of reactions which constitute the present invention may be obtained by bringing alcoholic hydrogen chloride into intimate contact with Compound B (free base) prepared as subsequently outlined and more fully described in the aforementioned copending application U.S. Ser. No. 76,495 and South African Patent 87/6400, the teachings of which are incorporated by reference. The crystalline hydrochloride salt which forms may be recovered by filtration, washed and dried in a conventional way.

In the process of the present invention, the first step of reacting Compound B as the bis-hydrochloride with carbonyldiimidazole is carried out by adding Compound B.2HCl to a reaction medium containing carbonyldiimidazole and a hydrogen chloride acceptor in solution in an inert solvent at a temperature in the range of about 15° to 50° C., preferably ambient temperature, for up to several hours until the reaction is substantially complete. The completion of the reaction may be determined by liquid chromatography.

The carbonyldiimidazole is employed in substantial molar excess. Generally, from about three- to five-fold molar excess is satisfactory.

A strong base is desired as the hydrogen chloride acceptor. Many of the conventional tertiary amines are not completely satisfactory. Suitable hydrogen chloride acceptors include 1,8-diazabicyclo-[5.4.0] undec-7-ene; 1,5-diazabicyclo[4.3.0]non-5-ene; and [1,8-bis(dimethylamino)-naphthalene, N,N,N', N'-tetramethyl-1,8-naphthalene] ("proton sponge"); and other strong bases. Imidazole also may be employed but tends to produce lower yields.

The reaction is carried out in a solvent. Suitable solvents include tetrahydrofuran, dioxane, dimethylformamide, dimethyl sulfoxide, acetonitrile and the like. Chlorinated solvents are generally not satisfactory because of the relatively low solubility of the reactant in the chlorinated solvents.

After completion of the reaction, the reaction mixture is concentrated under reduced pressure and to the concentrated solution are added a water-immiscible organic solvent and deionized water and the components of the reaction mixture partitioned. The organic product layer is then washed, preferably with brine and then concentrated under reduced pressure to form crystals of Compound D in the concentrated mixture. The resulting slurry is flushed into a non polar solvent, cooled and aged to obtain the desired intermediate Compound D, a novel compound, as a crystalline solid.

The second step of the process of the present invention is carried out by charging a high pressure hydrogenation vessel with Raney nickel catalyst, methanol solvent, sodium methoxide and Compound D, introducing hydrogen and then maintaining the temperature and pressure at 50° C.±1° C. and 40 psig until the reaction is substantially complete.

After completion of the hydrogenation, the vessel is cooled to ambient temperature, the catalyst removed and washed, and the filtrates combined and concentrated. Methylene chloride and saturated sodium bicarbonate solution are added. After a short (few minutes) aging period, the organic and aqueous layers are separated, and the organic layer concentrated to obtain Compound I as a slurry. The slurry is washed with methanol, and concentrated.

To a separate vessel charged with methanol and acetyl chloride and maintained below about 20° C. for in situ generation of hydrogen chloride, is added the methanolic slurry of Compound I. The slurry is then aged first at 20°-25° C. and thereafter at about 0° C. to complete the formation of the hydrochloride of Compound I. The slurry is then filtered washed and dried to obtain Compound I'.HCl product.

A compound particularly useful in the treatment of diabetes, (2R-trans)-N-[2-(1,3,4,6, 7,12b-hexahydro-2'-oxospiro[2H-benzofuro[2,3-a]-quinolizine-2,4'-imidazolidin]-3'-yl)ethyl]methanesulfonamide, may be produced facilely by this method which as applied to this compound comprises the steps of:

(1) intimately contacting (2R,trans)-N-[2-[(2-cyano-(1,3,4,6,7,12b-hexahydro-2H-benzofuro[2,3-a]quinolizin-2-yl)amino]ethyl]methanesulfonamide-bis-hydrochloride with carbonyldiimidazole in the presence of 1,8-diazabicyclo[5.4.0]undec-7-ene to obtain (trans)-1,3,4,6,7,12b-hexahydro-2-[3-(methylsulfonyl)-2-oxo-1-imidazolidinyl]-2H-benzofuro[2,3-a]-quinolizine-2-carbonitrile; and (2) intimately contacting said (trans)-1,3,4,5,7,12b-hexahydro-2-[3-(methylsulfonyl)-2-oxo-1-imidazolidinyl]2H-benzofuro[2,3-a]quinolizine-2-carbonitrile with hydrogen in the presence of Raney nickel catalyst to obtain (2R-trans)-N-[2-(1,3,4,6,7,12b-hexahydro-2'-oxospiro[2H-benzofuro-[2,3a]-quinolizine-2,4'-imidazolidin]-3'-yl)ethyl]-methanesulfonamide and thereafter intimately contacting the methanesulfonamide with a mixture acetyl chloride and methanol to obtain the monohydrochloride salt thereof.

The following example illustrates the invention but is not to be construed as limiting.

EXAMPLE I (2R-trans)-N-(2-(1,3,4,6,7,12b-hexahydro-2'-oxospiro(2H-benzofuro(2,3-A)quinolizine-2,4'-imidazolidin)-3'-yl)ethylmethanesulfonamide (Compound I')

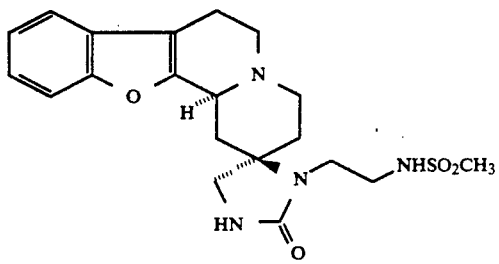

Part A. Preparation of (trans)-1,3,4,6,7,12b-hexahydro-2-[3-(methylsulfonyl)-2-oxo-1-imidazolidinyl]-2H-benzofuro[2,3-a]-quinolizine-2-carbonitrile (Compound D')

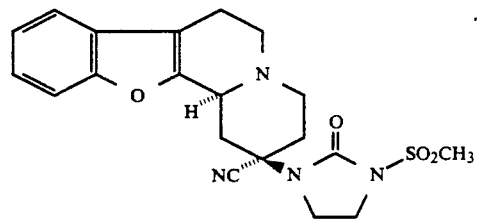

7.5 kg of carbonyldiimidazole was charged to 95 kg of dried tetrahydrofuran and the mixture aged at 25±2° C. for 10 minutes. 3.6 kg of 1,8-diazabicyclo[5.4.0]undec-7-ene was pumped thereinto followed by a pump and line rinse with 3-5 liters of tetrahydrofuran. 5.3 kg of (2R-trans)-[2-[(2-cyano-1,3,4,6,7,12b-hexahydro-2H-benzofuro[2,3a]quinolizine-2-yl)-amino]ethyl]methanesulfonamide bis-hydrochloride, (Compound B'● bis HCl) was added as a solid and the mixture aged at about 25° C. for two hours to produce Compound D' in the reaction mixture. When the reaction is substantially complete as determined by liquid chromatography, the reaction mixture was vacuum concentrated at 35° C./50 mm Hg to a volume of 10 gallons. To the concentrate was added 240 kg of ethyl acetate and 28 gallons of deionized water and the concentrate partitioned to recover the intermediate Compound D' in the organic layer. The organic solution was washed twice with saturated sodium chloride solution and vacuum concentrated at 30° C./50 mm Hg to 10 gallons.

The concentrate was flushed with 300 kg of ethyl acetate to KF=80 mcg/ml (Karl Fischer assay) and then vacuum concentrated at 30° C./50 mm Hg to 15 gallons. Crystallization of the intermediate (Compound D) occurred during the flush. The slurry was flushed into 210 kg hexane, vacuum concentrated at 30° C./50 mm Hg to a final volume of 25 gallons, and then cooled to about 0° C., aged for one hour and then filtered. The filter cake was washed with 14 kg hexane and vacuum dried at 25° C. to a loss on drying of less than 0.1 percent. The yield of Compound D' was 4.8 kg or 91 percent of theoretical.

The NMR spectra of the compound are as follows:

$^1$H NMR (CDCl$_3$, 300 MHZ) δ 7.35–7.50 (m,2H), 7.15–7.32 (m,2H), 3.80–3.95 (m,2H), 3.69 (dd, J=11.9, 2.1 Hz), 3.55–3.65 (m,2H), 3.34 (s,3H), 2.55–3.23 (m, 8H) 2.14 (dt, 1H, J=4.5, 12.8 Hz), 1,91 (t, 1H, J=12.8).

$^{13}$C NMR (CDCl$_3$) δ 154.5, 154.1, 150.6, 127.6, 123.7, 122.6, 118.8, 117.5, 111.7, 111.1, 55.9, 55.1, 51.3, 50.7, 40.8, 40.5, 40.3, 35.6, 33.4, 20.9.

Part B. Preparation of Compound I'

10 kg of Raney nickel catalyst previously dehydrated via methanol decantation was charged to a hydrogenation bomb. Thereafter 190 kg methanol was charged via residual vacuum, followed by 1.3 kg sodium methoxide and 4.8 kg Compound D'. The bomb was pressure tested at 50 psig with nitrogen then hydrogen was introduced and hydrogenation was carried out at 50±1° C./40 psig until the reaction was complete (about 5 hours).

The bomb was cooled to 25° C., the catalyst filtered, and the filter cake washed with 75 kg of methanol. The combined filtrate was then vacuum concentrated at 60° C./50 mm Hg to a volume of 12 gallons.

308 kg of methylene chloride and 63 kg of saturated sodium bicarbonate solution were added to the concentrated, the mixture aged for 5 minutes at 20°–25° C. and the layers separated. The organic product layer was flushed with 120 kg of methylene chloride to KF=1 mg/ml and then vacuum concentrated at 25° C./50 mm Hg to a volume of 12 gallons.

The concentrate was then flushed with 72 kg of methanol and vacuum concentrated at 30° C./50 mm Hg to a volume of 12 gallons. The concentrate was recovered, the vessel rinsed with 3 to 5 liters of methanol and the rinse separately saved.

A separate vessel was charged with 15 kg methanol and 1.0 kg of acetyl chloride while maintaining the temperature at less than 20° C. for an in situ generation of hydrogen chloride. To the vessel then was charged the methanolic solution of the hydrogenation product followed by a methanol rinse. The resulting slurry was aged at 20°–25° C. for one-half hour, then cooled to about 0° C. and aged for an additional two hours.

At the end of this period the slurry was filtered, the filter cake washed with 9 kg methanol and the cake dried at 25° C. to a loss on drying of less than 71%. The yield of the product was 3.2 kg or 71 percent.

EXAMPLE II (2R-Trans)-N-(2-(1,3,4,6,7,12b-hexahydro-2'-oxos-piro(2H-benzothieno(2,3-a)quinolizine-2,4'-imidazolidin)-3'-yl)ethylmethanesulfonamide hydrochloride (Compound I'')

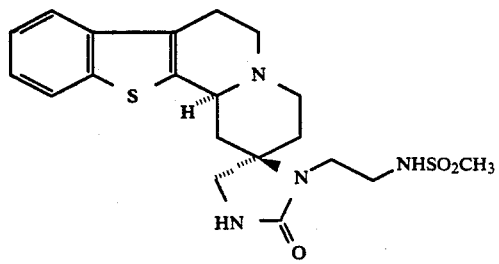

Part A. Preparation of (trans)-1,3,4,6,7,12b-hexahydro-2-[3-(methylsulfonyl)-2-oxo-1-imidazolidinyl]-2H-benzofuro[2,3-a]-quinolizine-2-carbonitrile (Compound D'')

In an operation carried out in a manner similar to that described in Example I, 5.5 kg of (2R-trans)-[2-[(2-cyano-(1,3,4,6,7,12b-hexahydro-2H-benzothieno(2,3-a)quinolizine-2-yl)-amino]ethyl]-methanesulfonamide bis-hydrochloride is added to mixture of 7.5 kg of carbonyldiimidazole in 95 kg of tetrahydrofuran and 1,8-diazabicyclo [5.4.0]undec-7-ene and the resulting mixture allowed to stand at ambient temperature to obtain Compound D''. The reaction mixture is concentrated and then partitioned between ethyl acetate and water to recover Compound D'' in the organic layer.

Part B. Preparation of Compound I''

4.5 kg of Compound D'' is added to a hydrogenation bomb containing 10 kg Raney nickel catalyst and 190 kg methanol and hydrogenation carried out at 50° C. at 40 psig until the reaction is complete to obtain Compound D''.

Compound D'' is separated from the catalyst, the filtrate concentrated and 308 kg methylene chloride and 63 kg of saturated sodium bicarbonate added thereto and thoroughly mixed and they hydrogenation product recovered from methylene chloride solution and concentrated in the manner described in Example I.

The hydrogenation product is then added to the HCl generation mixture of acetyl chloride and methanol to obtain the desired Compound I''.

EXAMPLE III

In a manner similar to that described in the preceding examples, the following compounds may be prepared:
(1) (2R-trans)-N-(2-(1,3,4,6,7,12b-hexahydro-2'-oxos-piro(2,3-a)quinolizine-2,4'-imidazolidin)-3'-yl)ethyl-methanesulfondamide
(2) (2R-trans)-N-(2-(1,3,4,6,7,12b-hexahydro-2'-oxos-piro(benzo(2,3-a)quinolizine-2,4'-imidazolidin)-3'-yl)ethylmethanesulfondamide

PREPARATION OF STARTING MATERIALS

The starting material (Compound A) may be prepared by the following sequence of reactions as described in the aforecited South African patent 87/6400 and also in U.S. Pat. No. 4,710,504, Dec. 1, 1987, the teachings of which are incorporated by reference.

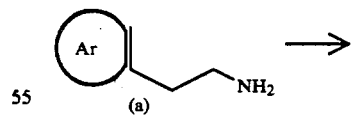
(a)

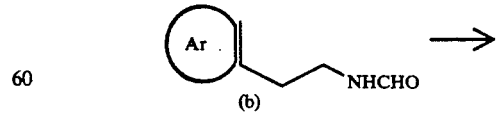
(b)

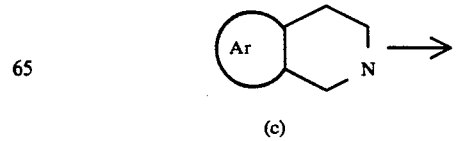
(c)

-continued

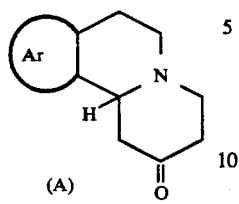
(A)

In carrying out the foregoing process, the aminomethyl compound (a) is heated with ethyl formate at about 60° C. for several hours, the reaction mixture then poured into dilute hydrochloric acid, the resulting mixture extracted with methylene chloride, the extract purified, dried, and the solvent evaporated to obtain the formamido compound (b). The latter is added to a strong acid or to a dehydrating agent such as polyphosphoric acid, phosphorus pentoxide, or methane sulfonic acid at 100° C. and the mixture heated for 1-2 hours to obtain an Ar-condensed dihydropyridine compound (c) which may be recovered by conventional procedures. Compound (c) may than be converted to the quinolizin-2-one (A) by adding 2-trimethylsilyloxy-1,3-butadiene, then zinc chloride, heating the mixture at 60° C. for 1-2 hours and thereafter recovering by conventional procedures.

What is claimed is:

1. A compound of the formula

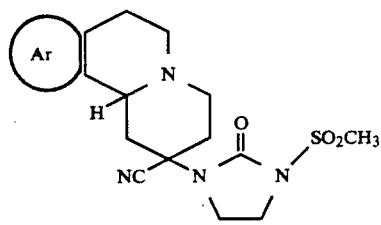

where

is $R^1$, $R^2$-benzo furo or $R^1$, $R^2$-benzo(b)thieno, wherein $R^1$ and $R^2$ are independently hydrogen, halo, hydroxy, $C_{1-3}$ alkoxy, lower alkyl, or carboxy, or together are methylenedioxy or $C_{3-4}$ alkylene; and wherein the free bonds of

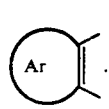

are attached in either configuration of

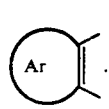.

2. A compound of the formula

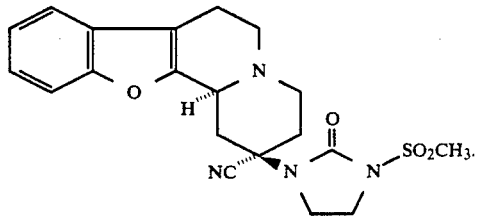

* * * * *